United States Patent
He et al.

(10) Patent No.: US 10,052,620 B2
(45) Date of Patent: Aug. 21, 2018

(54) CATALYST FOR OXIDATION REACTIONS, A METHOD FOR ITS PREPARATION AND THE USE THEREOF

(71) Applicants: Chuanhua He, Jiangsu (CN); Benjamin Fonfe, Frankfurt (DE); Harald Jakob, Hasselroth (DE); Xiangyu Yang, Beijing (CN)

(72) Inventors: Chuanhua He, Jiangsu (CN); Benjamin Fonfe, Frankfurt (DE); Harald Jakob, Hasselroth (DE); Xiangyu Yang, Beijing (CN)

(73) Assignee: EVONIK DEGUSSA GmbH, Essen (DE)

(*) Notice: Subject to any disclaimer, the term of this patent is extended or adjusted under 35 U.S.C. 154(b) by 260 days.

(21) Appl. No.: 15/102,842

(22) PCT Filed: Dec. 4, 2014

(86) PCT No.: PCT/EP2014/076536
§ 371 (c)(1),
(2) Date: Jun. 8, 2016

(87) PCT Pub. No.: WO2015/086424
PCT Pub. Date: Jun. 18, 2015

(65) Prior Publication Data
US 2018/0133704 A1    May 17, 2018

(30) Foreign Application Priority Data

Dec. 11, 2013   (WO) ............... PCT/CN2013/089142

(51) Int. Cl.
C07C 309/00   (2006.01)
B01J 31/02    (2006.01)
B01J 37/04    (2006.01)
B01J 37/03    (2006.01)
C07C 303/16   (2006.01)
C07C 319/24   (2006.01)
B01J 37/02    (2006.01)

(52) U.S. Cl.
CPC ....... B01J 31/0239 (2013.01); B01J 37/0236 (2013.01); B01J 37/031 (2013.01); B01J 37/04 (2013.01); C07C 303/16 (2013.01); C07C 319/24 (2013.01); B01J 2231/70 (2013.01); B01J 2531/004 (2013.01)

(58) Field of Classification Search
CPC .. B01J 31/0239; B01J 37/0236; B01J 37/031; B01J 37/04; B01J 2231/70; B01J 2531/004; C07C 319/24; C07C 303/16
See application file for complete search history.

(56) References Cited

U.S. PATENT DOCUMENTS

| 8,501,657 B2 | 8/2013 | Li et al. | |
| 2011/0015060 A1* | 1/2011 | Li | B01J 27/188 502/164 |

FOREIGN PATENT DOCUMENTS

| CN | 101 081 994 A | 12/2007 |
| CN | 101081994 | * 12/2007 |
| CN | 102430428 A | 5/2012 |
| CN | 102 600 903 A | 7/2012 |
| CN | 102600903 | * 7/2012 |
| WO | 2009/117862 A1 | 10/2009 |

OTHER PUBLICATIONS

CN101081994 translated (Year: 2007).*
CN102600903 translated (Year: 2012).*
International Search Report and Written Opinion dated Feb. 10, 2015 in PCT/EP2014/076536 filed Dec. 4, 2014.
International Search Report and Written Opinion dated Sep. 1, 2014 in PCT/CN2013/089142 filed Dec. 11, 2013.

* cited by examiner

Primary Examiner — Yevgeny Valenrod
Assistant Examiner — Blaine G Doletski
(74) Attorney, Agent, or Firm — Oblon, McClelland, Maier & Neustadt, L.L.P.

(57) ABSTRACT

The present invention relates to a catalyst for oxidation reactions, particularly for oxidation of mercaptan dialkyldisulfides and/or dialklypolysulfides with oxygen to alkanesulfonic acids.

22 Claims, No Drawings

CATALYST FOR OXIDATION REACTIONS, A METHOD FOR ITS PREPARATION AND THE USE THEREOF

The present invention relates to a catalyst for oxidation reactions, particularly for oxidation of mercaptan dialkyldisulfides and/or dialkylpolysulfides with oxygen to alkanesulfonic acids.

Alkanesulfonic acids, also referred to as alkylsulfonic acids, are strong, non-oxidizing acids which can be used for example as catalysts in alkylation, esterification and polymerization reactions. These acids can be produced by oxidation of sulfur containing hydrocarbon compounds such as alkylmercaptans, dialkyldisulfides and/or dialkylpoly-sulfides. One of the most important alkanesulfonic acids is methanesulfonic acid, also referred to as MSA. This particular acid is widely used in surfactants, polymer additives and for different purposes in the pharmaceutical industry. Its relevance is illustrated through the capacity of its production: The capacity for the production of MSA reached 40,000 tons per year in 2008, and the demand for MSA is still continuously increasing.

Several different methods for the production of alkanesulfonic acids are known. For example, the patent documents U.S. Pat. Nos. 3,600,136; 3,626,004; 3,993,692; EP 313939 B1; EP 675106 B1 and the published patent applications GB 1,350,328 A and EP 424616 A2 disclose processes for the production of alkanesulfonic acids by hydrolysis of alkanesulfonyl chloride, which is prepared by oxidation of sulfur containing organic compounds, such as thiols, sulfites and disulfides, with chlorine. The disadvantages of these processes are that (i) they use chlorine, a highly corrosive gas, as oxidant, which leads to high investment costs for the corrosive-resistant equipment, (ii) the alkanesulfonic acids obtained by this method are generally intensively coloured, which requires additional bleaching steps to remove the colorizing portions, and (iii) the hydrolysis of alkanesulfonyl chlorides gives hydrochloric acid as undesired by-product, another highly corrosive substance.

The U.S. Pat. Nos. 2,433,395; 2,433,396; 2,502,591; 2,697,722 and 2,727,920 disclose processes for the production of alkanesulfonic acids by oxidation of alkylmercaptans or dialkyldisulfides with oxygen in the presence of nitrogen oxides or nitric acid:

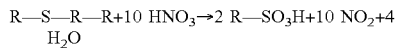
R—S—R—R+10 HNO$_3$→2 R—SO$_3$H+10 NO$_2$+4 H$_2$O

When nitric acid is used, the formed nitrogen dioxide is regenerated with oxygen and water to nitric acid, which is thus available for further oxidation of the dialkyldisulfide to the alkanesulfonic acid:

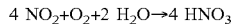
4 NO$_2$+O$_2$+2 H$_2$O→4 HNO$_3$

The disadvantage of the processes of these documents is that they (i) involve large amounts of water, which must be separated from the alkanesulfonic acid by cost and energy intensive distillation, (ii) the oxidation of the sulfur containing compound proceeds rather severely, and (iii) the crude alkanesulfonic acids contain undesired colorizing and odorizing bodies, which must be removed from the desired product by further purifying steps.

U.S. Pat. No. 6,531,629 discloses a process the preparation of alkanesulfonic acids in which alkylmercaptans and/or dialkylpolysulfides are oxidized with nitric acid. The nitrogen oxides NO$_x$, formed as by-products, are regenerated to nitric acid and recycled into the first reaction step to further oxidize alkylmercaptans and/or dialkylpolysulfides. In this way the overall yield for the formation of alkanesulfonic acids is improved. Since this process uses nitric acid as oxidizing agent, over-stoichiometric amounts of nitric acid and a high concentration of the nitrogen oxides are present in the reaction mixture. Therefore, corrosive-resistant reactor materials are required, which leads to high investment costs. Further, nitrogen oxides are unhealthy and environmentally harmful. Accordingly an additional cost intensive treatment of the nitrogen oxides containing off-gases is necessary in order to avoid the exposure of nitrogen oxides to the environment.

The patents U.S. Pat. Nos. 4,910,330; 4,987,250; and EP 854136 B1 each disclose the production of alkanesulfonic acids by oxidation of alkylmercaptans with hydrogen peroxide. Since hydrogen peroxide is normally used as a solution of 30 percent by weight in water, large amounts of water are introduced into the reaction, which after completion of the reaction must be distilled off from the crude alkanesulfonic acid. It is therefore a disadvantage of this process that a high energy input is required in order to provide water-free alkanesulfonic acids. An additional disadvantage of this process is the complicated reaction control: Alrefa a very small excess of hydrogen peroxide may result in a quite varying yield and purity of th desired alkanesulfonic acid. Therefore oxidant hydrogen peroxide and the starting material alkylmercaptan must be simultaneously fed into the reaction within a very narrow molar ratio, which however is hard to control.

U.S. Pat. No. 5,608,103 discloses a process for the production of alkanesulfonic acids by photo-oxidation of sulfur-containing derivatives. However, this process is not suitable for industrial scale production of alkanesulfonic acids.

Accordingly, there is a need for a catalyst system to facilitate the oxidation of sulfur containing hydrocarbon compounds with oxygen to the corresponding alkanesulfonic acids and in particular, for the oxidation of alkylmercaptans, dialkyldisulfides and/or dialkylpolysulfides with oxygen to the corresponding alkanesulfonic acids.

The published patent application EP 0396934 A1 discloses a process for caustic-free sweetening of sour hydrocarbon streams, which contain mercaptans. In this process a mercaptan comprising hydrocarbon fraction is contacted with a catalytic composite, which is effective in oxidizing said mercaptans to disulfides in the presence of an oxidizing agent, an aqueous solution of ammonium hydroxide and a quaternary ammonium compound. Said catalytic composite comprises a metal chelate dispersed on an adsorbent support. However, the catalytic system of EP 0396934 A1 does not allow the production of alkanesulfonic acids from sulfur containing hydrocarbon compounds.

The published patent application CN 101081994 A discloses a process for the removal of sulfur from gasoline. In this process sulfur-containing organic compounds are oxidized to sulfone or SO$_2$ with hydrogen peroxide in the presence of a catalyst of the general formula Q$^+$[MW$_x$O$_y$]$^-$ in which Q is a quaternary ammonium cation, M is an alkali metal ion of for example sodium, potassium or lithium, an alkaline earth metal ion of for example magnesium or calcium, aluminum, a transition metal ion of for example copper, zinc, cadmium or nickel, or a rare earth metal ion of for example lanthanum, and W is molybdenum or tungsten. Also the published patent application US 2011/0015060 A1 discloses a catalyst for the desulfurization and desodorization of gasoline, which is represented by the formula: Q$_l$B$_m$H$_n$[A$_x$M$_y$O$_z$]$^{(l+m+n)-}$, where Q denotes a quaternary ammonium cation, B is Na$^+$ and/or K$^+$, H denotes a hydrogen atom, A is boron, phosphor, arsenic, silicon or aluminum, M is tungsten or molybdenum, and O denotes an oxygen atom. However, the catalysts of CN 101081994 A and US 2011/0015060 A1 only show a poor catalytic activity in the oxidation of methylmercaptan or dimethyldisulfide with oxygen. Accordingly, these catalysts are not suitable for use in the industrial preparation of alkanesulfonic acids.

It is therefore an object of the present invention to provide a more efficient catalyst for the oxidation of sulfur containing hydrocarbon compounds, preferably of methylmercaptan and/or dimethyldisulfide, with oxygen to alkanesulfonic acids.

It was found that the replacement of tungsten in the aforementioned catalysts with vanadium significantly changes the activity of the thus obtained catalyst with respect to the oxidation of sulfur containing hydrocarbon compounds.

One object of the present invention is therefore a catalyst according to the general formula (I)

$$Q_a[M_b(VO_4)_c]^{a-} \quad (I),$$

wherein
Q is a quaternary ammonium cation of the general formula (II)

$$R^1R^2R^3R^4N^+ \quad (II),$$

wherein each of $R^1$, $R^2$, $R^3$ and $R^4$ is independently of each other a saturated $C_1$ to $C_{20}$ alkyl radical or an aromatic $C_5$ or $C_6$ radical with the proviso that at least one of $R^1$, $R^2$, $R^3$ and $R^4$ is a saturated $C_4$ to $C_{20}$ alkyl group,
M is at least one metal selected from the group consisting of alkali metals, alkaline earth metals, group III metals and transition metals,
V denotes vanadium,
O denotes oxygen,
a is an integer from 1 to 3,
b is the integer 1 or 2,
and
c is the integer 1 or 2.

Depending on the valence of the specific metal M the number of vanadate ions and ammonium cations Q in the catalyst of the present invention varies. Thus, in context of the present invention, a is the integer 1, 2 or 3, preferably a is the integer 1 or 3, b is the integer 1 or 2 and c is the integer 1 or 2.

In contrast to the tungsten and molybdenum based catalysts known from the prior art, the catalyst of the present invention shows a significantly increased activity for the catalysis of oxidation reaction, especially for the oxidation of sulfur containing hydrocarbon compounds, preferably for alkylmercaptan, dialkyldisulfides and/or dialkylpolysulfides.

The catalyst of the present invention leads to high conversion rates of the starting compound and to high yields for the product. More specifically, the use of this catalyst gives only small amounts of by-products such as sulfuric acid. In addition, the catalyst of the present invention only require mild reaction conditions, for example the use of oxygen as oxidizing agent. Therefore, the catalyst of the present invention is suitable for industrial use.

In principle, a catalyst of the present invention, in which each of the radicals $R^1$ to $R^4$ is independently from each other either a saturated $C_4$ to $C_{18}$ alkyl group or a methyl group, can be used in the oxidation of alkylmercaptans, dialkyldisulfides and/or dialkylpolysulfides.

Therefore, in one embodiment of the present invention Q is a quaternary ammonium cation according to the general formula (III)

$$(C_nH_{2n+1})_o(CH_3)_{4-o}N^+ \quad (III),$$

wherein
n is an integer from 4 to 18, and
o is an integer from 1 to 4.

In the context of the present invention o comprises all integers from 1 to 4, which are 1, 2, 3, and 4. In the context of the present invention n comprises all integers from 4 to 18, i.e., the integers 4, 5, 6, 7, 8, 9, 10, 11, 12, 13, 14, 15, 16, 17, and 18. Preferably, n is the integer 4, 8, 12, 16 or 18, especially n is the integer 16.

Therefore, in a preferred embodiment of the present invention Q is selected from the group of quaternary ammonium cations consisting of $(C_4H_9)_4N^+$, $(C_4H_9)_3(CH_3)N^+$, $(C_4H_9)_2(CH_3)_2N^+$, $(C_4H_9)(CH_3)_3N^+$, $(C_8H_{17})_4N^+$, $(C_8H_{17})_3(CH_3)N^+$, $(C_8H_{17})_2(CH_3)_2N^+$, $(C_8H_{17})(CH_3)_3N^+$, $(C_{12}H_{25})_4N^+$, $(C_{12}H_{25})_3(CH_3)N^+$, $(C_{12}H_{25})_2(CH_3)_2N^+$, $(C_{12}H_{25})(CH_3)_3N^+$, $(C_{16}H_{33})_4N^+$, $(C_{16}H_{33})_3(CH_3)N^+$, $(C_{16}H_{33})_2(CH_3)_2N^+$, $(C_{16}H_{33})(CH_3)_3N^+$, $(C_{18}H_{37})_4N^+$, $(C_{18}H_{27})_3(CH_3)N^+$, $(C_{18}H_{37})_2(CH_3)_2N^+$, $(C_{18}H_{37})(CH_3)_3N^+$ and $((C_{18}H_{37})_{75\%}(C_{16}H_{33})_{25\%})_2(CH_3)_2N^+$.

It was also found that good yields for the formation of alkanesulfonic acids are in particular achieved, when the quaternary ammonium cation in the catalyst contains at least one saturated $C_{16}$ alkyl radical.

Therefore, in a further preferred embodiment of the present invention Q is $(C_{16}H_{33})_4N^+$, $(C_{16}H_{33})_3(CH_3)N^+$, $(C_{16}H_{33})_2(CH_3)_2N^+$ Or $(C_{16}H_{33})(CH_3)_3N^+$.

By far the best results for the production of alkanesulfonic acids were obtained, when the quaternary ammonium cation in the catalyst contains at least one saturated $C_{16}$ alkyl radical and a methyl radical. The most efficient catalyst contains one saturated $C_{16}$ alkyl radical and three methyl groups in its quaternary ammonium cation.

Therefore, the quaternary ammonium cation Q in the catalyst of the present invention is preferably $(C_{16}H_{33})(CH_3)_3N^+$.

According to the present invention the metal M in the catalyst of the present invention is an alkali metal, alkaline earth metal, group III metal and/or a transition metal. In general, the catalyst of the present invention is not subjected to any limitations regarding the specific choice of the alkali metal, alkaline earth metal, group III metal and/or a transition metal for the metal M. Non-limiting examples of the metal M are Na, K, Ba, Mg, Ca, Co, Cu, Fe, Zr and Al.

It was found that the presence of a metal M, which is selected from Mg, Co, Cu, Fe, Ba and Z, in the catalyst of the present invention significantly contributes to their catalytic activity in the oxidation of sulfur containing hydrocarbon compounds with oxygen, for example in the oxidation of dimethyldisulfide as an exemplary representative of the dialkyldisulfides.

Therefore, in one embodiment of the present invention M is a metal selected from the group consisting of Mg, Co, Cu, Fe, Ba and Zr.

In the oxidation of dimethyldisulfide, as a representative dialkydisulfide, catalyst in which the metal M is Mg showed the highest conversion rate for the sulfur containing starting compound and the highest yield for the desired alkanesulfonic acid.

Therefore, in a preferred embodiment of the present invention the metal M is Mg.

The catalyst according to the present invention comprises a vanadate ion $VO_4^{3-}$ and a quaternary ammonium cation Q of the formula $R^1R^2R^3R^4N+$, with the above identified definitions. Depending on the valence of the metal ions comprised therein, the catalyst of the present invention comprises preferably one or two vanadate ions and one or three quaternary ammonium cations Q. The latter is for example the case when M is Al. However, with M being a metal selected from the group consisting of Mg, Co, Cu, Fe, Ba and Zr, the catalyst of the present invention comprises one vanadium ion and one quaternary ammonium cation Q.

Therefore, in another preferred embodiment of the present invention a is 1, b is 1 and c is 1.

Thus, the catalyst of the present invention preferably corresponds to the general formula (I)

$$Q[MVO_4]^- \qquad (I)$$

wherein

Q is selected from the group of quaternary ammonium cations consisting of $(C_4H_9)_4N^+$, $(C_4H_9)_3(CH_3)N^+$, $(C_4H_9)_2(CH_3)_2N^+$, $(C_4H_9)(CH_3)_3N^+$, $(C_8H_{17})_4N^+$, $(C_8H_{17})_3(CH_3)N^+$, $(C_8H_{17})_2(CH_3)_2N^+$, $(C_8H_{17})(CH_3)_3N^+$, $(C_{12}H_{25})_4N^+$, $(C_{12}H_{25})_3(CH_3)N^+$, $(C_{12}H_{25})_2(CH_3)_2N^+$, $(C_{12}H_{25})(CH_3)_3N^+$, $(C_{16}H_{33})_4N^+$, $(C_{16}H_{33})_3(CH_3)N^+$, $(C_{16}H_{33})_2(CH_3)_2N^+$, $(C_{16}H_{33})(CH_3)_3N^+$, $(C_{18}H_{37})_4N^+$, $(C_{18}H_{27})_3(CH_3)N^+$, $(C_{18}H_{37})_2(CH_3)_2N^+$, $(C_{18}H_{37})(CH_3)_3N^+$ and $((C_{18}H_{37})_{75\%}(C_{16}H_{33})_{25\%})_2(CH_3)_2N^+$, preferably Q is $(C_{16}H_{33})_4N^+$, $(C_{16}H_{33})_3(CH_3)N^+$, $(C_{16}H_{33})_2(CH_3)_2N^+$ or $(C_{16}H_{33})(CH_3)_3N^+$ and especially Q is $(C_{16}H_{33})(CH_3)_3N^+$, M is a metal selected from the group consisting of Mg, Co, Cu, Fe, Ba and Zr, preferably M is Mg, V is a vanadium atom, and O is an oxygen atom.

In general, the catalyst of the formula $C_{16}H_{33}(CH_3)_3N^+[MgVO_4]^-$ gives the best results in the catalysis of the oxidation of sulfur containing compounds.

Therefore, in a further preferred embodiment of the present invention the catalyst is a compound of the formula $C_{16}H_{33}(CH_3)_3N^+[MgVO_4]^-$.

The catalyst of the present invention can be used in oxidation reactions. Particularly, the catalyst of the present invention can be used in the oxidation of sulfur containing compounds such as sulfur containing hydrocarbons. Suitable sulfur containing hydrocarbons are those with an easily oxidizable sulfur containing group such a thiol group or a sulfur-sulfur group. Accordingly, suitable sulfur containing hydrocarbons are alkylmercaptans, dialkyldisulfides and dialkylpolysulfides. The catalyst of the present can either be used in the oxidation of a particular sulfur containing hydrocarbon compound or in the simultaneous oxidation of several sulfur containing hydrocarbon compounds.

Therefore, in another embodiment of the present invention the catalyst is suitable for oxidation reactions, preferably for the oxidation of sulfur containing hydrocarbon compounds, especially for the oxidation of alkylmercaptans, dialkyldisulfides and/or dialkylpolysulfides.

In context of the present invention alkylmercaptans correspond to the general formula R—SH, where R is a saturated alkyl group, dialkyldisulfides are compounds of the the general formula R—S—S—R or R—$S_2$—R, and dialkylpolysulfides have the general formula R—$S_n$—R, with n being an integer from 3 to 9. In context of the present of the present invention the two alkyl groups in a dialkyldisulfide and in dialkylpolysulfide are identical, in other words the dialkyldisulfide and the dialkylpolysulfide are symmetrical compounds. The alkyl radical R in each of the alkylmercaptans, dialkyldisulfides and dialkylpolysulfides is a saturated $C_1$ to $C_{20}$ alkyl group, preferably a $C_1$ to $C_{10}$ alkyl group, preferably a $C_1$ to $C_4$ alkyl group, such as a methyl, ethyl, n-propyl, iso-popyl, n-butyl, iso-butyl or tert-butyl group.

The catalyst of the present invention is obtainable by combining solutions of suitable precursor compounds or salts containing the specific elements or specific chemical entities of the desired catalyst. Typically, solutions of salts of the metal M in nitric acid are prepared at room temperature and stirred for a time which is sufficient for homogenizing the solution, e.g. 10 minutes. Suitable salts of the metal M are for example nitrate salts. Following, a salt of the quaternary ammonium cation Q, preferably a halogen salt, is added to the mixture and stirred for a time which is sufficient for homogenizing the solution, e.g. 30 minutes. Finally, a solution of an orthovanadate salt, preferably an alkali salt or alkaline earth salt of an orthovanadate, is added to the mixture, and the thus obtained mixture is stirred at room temperature for a time which is sufficient for homogenizing the solution, e.g. 24 hours. Alternatively, the sequence of adding the salt of the quaternary ammonium cation Q and the orthovanadate solution can be changed. Typically, the obtained mixture is concentrated under reduced pressure to give the catalytically active mass, which is finally dried.

Therefore, a further object of the present invention is a method for the production of the catalyst according to the present invention, which comprises the steps of a) providing a solution of a salt of the metal M in nitric acid, b) adding a salt of the quaternary ammonium cation Q to the solution obtained in step a), c) adding a solution of a salt of an orthovanadate to the solution obtained in step b), d) stirring the solution obtained in step c), e) concentrating the solution of step d) under reduced pressure to give a catalytically active mass, and f) drying the catalytically active mass obtained in step e).

As already mentioned above, the sequence of adding the salt of the quaternary ammonium cation Q (step b) and adding the solution of a salt of an orthovanadate (step c) can be changed. In other words, it is also possible to perform the step c) before the step b).

Therefore, in an alternative embodiment of the method for the production of the catalyst according to the present invention the sequence of the steps b) and c) is changed.

In general, the method of the present invention is not subjected to any limitations regarding the choice of the salt of the metal M. Thus, M is a metal selected from the group consisting of alkali metals, alkaline earth metals, group III metals and transition metals.

However, in accordance with the catalyst according to the present invention, the metal nitrate in step a) is preferably a nitrate of a metal, which is selected from the group consisting of Mg, Co, Cu, Fe, Ba and Zr.

According to the present invention the catalyst of the present invention and the catalyst obtainable and/or obtained by the method of the present invention are suitable for the catalysis of oxidation reactions, preferably, the catalysis of sulfur containing hydrocarbon compounds. Particularly, the catalyst of the present invention and the catalyst obtainable and/or obtained by the method of the present invention are suitable for the oxidation of alkylmercaptans to dialkyldisulfides and/or alkanesulfonic acids or the oxidation of dialkyldisulfides to alkanesulfonic acids or the oxidation of dialkylpolysulfides to alkanesulfonic acids with oxygen or hydrogen peroxide, preferably oxygen, as oxidizing agent in the presence or absence of nitric acid. Especially, the catalysts of the present invention are suitable for the oxidation of methylmercaptan to dimethyldisulfide and/or methanesulfonic acid, or the oxidation of dimethyldisulfide to methanesulfonic acid with oxygen or hydrogen peroxide, preferably oxygen, as oxidizing agent in the presence or absence of nitric acid.

Therefore, another object of the present invention is the use of a catalyst of the present invention or of a catalyst obtainable and/or obtained by a method of the present invention in the oxidation of sulfur containing hydrocarbon compounds.

In one embodiment of the use according to the present invention the oxidation reaction is the oxidation of alkylmercaptans to dialkyldisulfides and/or alkanesulfonic acids with oxygen or hydrogen peroxide as oxidizing agent in the presence or absence of nitric acid, or the oxidation of dialkyldisulfides to alkanesulfonic acids with oxygen or hydrogen peroxide as oxidizing agent in the presence or absence of nitric acid or the oxidation of dialkylpolysulfides to alkanesulfonic acids with oxygen or hydrogen peroxide as oxidizing agent in the presence or absence of nitric acid.

The commercially most relevant alkanesulfonic acid is methanesulfonic acid, which is obtainable by oxidation of dimethyldisulfide. The starting compound dialkyldisulfide can be obtained by oxidation of methylmercaptan and can thus be an intermediate product in the oxidation of methylmercatan to methanesulfonic acid.

Therefore, in a preferred embodiment of the use according to the present invention the oxidation reaction is the oxidation of methylmercaptan to dimethyldisulfide and/or methanesulfonic acid with oxygen or hydrogen peroxide as oxidizing agent in the presence or absence of nitric acid or the oxidation of dimethyldisulfide to methanesulfonic acid with oxygen or hydrogen peroxide as oxidizing agent in the presence or absence of nitric acid or the oxidation of dimethylpolysulfide to methanesulfonic acid with oxygen or hydrogen peroxide as oxidizing agent in the presence or absence of nitric acid.

Oxygen as oxidizing agent is easier to handle and also cheaper than hydrogen peroxide. A further advantage of oxygen as oxidizing agent is that it can be provided in different forms, for example as pure oxygen, as air or as air enriched with oxygen, i.e. with a content of at least 21 weight percent of oxygen, preferably more than 21 weight percent of oxygen.

It is therefore preferred that in the use of the present invention oxygen is the oxidizing agent.

In the context of the present invention, pure oxygen, air and air enriched with oxygen are each used in the sense of oxygen as oxidizing agent, if not otherwise stated.

The oxidation of a sulfur containing compound according to the use of the present invention is not subjected to any limitations regarding further components provide that they do not hinder the reaction, in particular that they do not decrease the conversion of the starting compound as well as yield and selectivity for the formation of the desired product. The presence of nitric acid in the use of the present invention is considered to have a beneficial effect on the oxidation of the sulfur containing hydrocarbon compounds. Therefore, the presence of nitric acid in the oxidation reaction is preferred in order to facilitate the oxidation according to the use of the present invention.

The catalytic activity of the catalyst of the present invention also allows to perform a process for oxidizing sulfur containing hydrocarbon compounds to alkanesulfonic acids. Typically, this process is performed in that a solution of the respective starting compound is placed in a reactor, the reactor is closed, oxygen or hydrogen peroxide is introduced into the reactor and the reaction mixture is stirred, thereby performing the reaction to obtain the desired product.

Therefore, a further object of the present invention is a process for the preparation of alkanesulfonic acids comprising the steps of
a) providing a solution comprising a sulfur containing hydrocarbon compound and a catalyst according to the present invention or a catalyst obtainable and/or obtained by a method of the present invention in an organic solvent,
b) introducing oxygen or hydrogen peroxide into the reaction system, and
c) stirring the resulting mixture.

Optionally, where appropriate, a stoichiometrically equivalent amount of water is added, preferably in step a). Water may be added as reactant in the reaction in order to give the desired alkanesulfonic acid. Preferably, water, if required, is added in an amount to hydrolyze the final reaction products of the alkylmercaptans, dialkyldisulfides or dialkylpolysulfides to the desired alkanesulfonic acids. In this way the conversion of starting material into the desired product is significantly increased. For example, when dimethyldisulfide is oxidized to methanesulfonic acid with oxygen in the presence of the catalyst of the present invention, it is preferred to add water to establish a molar ratio of dimethyldisulfide to $H_2O$ of 1:1.

Therefore, in one embodiment of the process of the present invention water, if required, is added in an amount which is sufficient to give the desired alkanesulfonic acid.

According to the present invention the catalyst of the present invention are particularly suitable for the oxidation of methylmercaptan to dimethyldisulfide and/or methanesulfonic acid or the oxidation of dimethyldisulfide to methanesulfonic acid.

Therefore, in one embodiment of the process of the present invention the sulfur containing hydrocarbon compound is methylmercaptan or dimethyldisulfide.

In general, the process of the present invention can be performed with or without nitric acid. However, additional nitric acid facilitates the oxidation of the sulfur containing hydrocarbon compound. Therefore, it is preferred to perform the process of the present invention is performed in the presence or absence of nitric acid.

It is particularly preferred to perform the process of the present invention with oxygen as oxidizing agent. Replacing the oxidizing agent hydrogen peroxide with oxygen has the advantage that it is less corrosive, less expensive and more conveniently to use than hydrogen peroxide.

In general, the process of the present invention is not subjected to any limitations regarding the solvent which is used for providing the solution of step a), provided that this solvent is inert under the reaction condition of this process, i.e. that it does not participate in the reaction and is left unmodified after the process.

Therefore, in one embodiment of the process of the present invention the organic solvent is selected from optionally substituted alkanes, preferably halogenated alkanes, optionally substituted aromatic hydrocarbons, preferably halogenated aromatic hydrocarbons, esters, ethers, ketones, alcohols, carboxylic acids, nitriles amides, sulfones, sulfoxides, alkanesulfonic acids and combinations thereof.

Preferably, said organic solvent is selected from benzene, toluene, chlorobenzene, dichlorobenzene, trichlorobenzene, nitrobenzene, sulfo lane, methylisobutyl ketone, dimethylsulfoxide, dimethylformamide, acetic acid, acetonitrile and combinations thereof. It is particularly preferred that the organic solvent is acetonitrile. The use of acetonitrile as solvent has the advantage that the product can be conveniently separated from by distillation or rectification. Thus, less energy is required and in addition, the solvent acetonitrile can be reused in the process of the present invention.

Generally, the process of the present invention is not subjected to any limitations regarding the temperature and/or the pressure at which the process is performed, provided that both are sufficiently high so that the process works. Typically, the pressure of the reaction is equivalent to the pressure of oxygen, in other words the pressure at which the reaction mixture is pressurized with oxygen. The lower limit of the reaction temperature is typically governed by the solubility of the reactant or the sulfur containing hydrocarbon compound and the upper limit of the reaction temperature is generally governed by the boiling point of the used solvent.

In one embodiment of the process of the present invention the process is performed at a pressure of from 10 bar to 120 bar.

Preferably, the pressure is from 20 bar to 80 bar, more preferably from 30 bar to 60 bar and especially at about 40 bar.

In another embodiment of the process of the present invention the process is performed at a temperature of from 40° C. to 150° C.

Preferably, the reaction temperature is from 50° C. to 100° C., especially from 60° C. to 90° bar.

EXAMPLES

I. Preparation of the Catalysts

Example 1

Preparation of $C_{16}H_{33}(CH_3)_3N^+[MgVO_4]^-$ (Mg—V catalyst)

Magnesium nitrate hexahydrate (0.53 g) and a solution of nitric acid (30 ml, 0.1 mol/l) were placed in a 100 l flask. The thus obtained mixture was stirred for 30 minutes and afterwards, hexadecyltrimethylammonium chloride (0.33 g) was added to this mixture and the resulting suspension was stirred for another 60 minutes. To this suspension, a solution of sodium orthovanadate dodecahydrate (4 g) in nitric acid (20 ml, 0.1 g/l) was added and the resulting mixture was stirred at room temperature for 24 hours. Subsequently, the mixture was concentrated under reduced pressure using a rotary evaporator and dried at 100° C. for 4 hours.

Example 2

Preparation of $C_{16}H_{33}(CH_3)_3N^+[CoVO_4]^-$ (Co—V catalyst)

Cobalt nitrate hexahydrate (2.33 g) was dissolved in nitric acid (120 ml, 0.1 mol/l) at room temperature. The resulting solution was placed in a 500 ml flask and stirred for 10 minutes. Subsequently, a solution of sodium orthovanadate dodecahydrate (16 g) in water (80 ml) was added and the thus obtained suspension was stirred for 30 minutes. To this suspension, hexadecyltrimethylammonium chloride (1.28 g) was added and the resulting mixture was stirred at room temperature for 24 hours. Afterwards, the mixture was concentrated under reduced pressure using a rotary evaporator and dried at 100° C. for 4 hours.

Example 3

Preparation of $C_{16}H_{33}(CH_3)_3N^+[CuVO_4]^-$ (Cu—V catalyst)

The Cu—V catalyst was prepared using the procedure of example 2, except that cobalt nitrate hexahydrate was replaced with cupric nitrate hydrate (1.93 g).

Example 4

Preparation of $C_{16}H_{33}(CH_3)_3N^+[FeVO_4]^-$ (Fe—V catalyst)

Iron(III) nitrate nonahydrate (4 g) was placed in a 100 ml flask, dissolved in nitric acid (30 ml, 0.1 mol/l) at room temperature and the resulting solution stirred for 30 minutes. A solution of sodium orthovanadate dodecahydrate (4 g) in water (20 ml) was added and the resulting suspension was stirred for another 30 minutes. To this suspension, hexadecyltrimethyl-ammonium chloride (0.32 g) was added and the thus obtained mixture was stirred at room temperature for 24 hours. This mixture was concentrated under reduced pressure using a rotary evaporator and dried at 100° C. for 4 hours.

Example 5

Preparation of $C_{16}H_{33}(CH_3)_3N^+[BaVO_4]$ (Ba—V catalyst)

Barium chloride dihydrate (0.84 g) was placed in a 250 ml flask, dissolved in nitric acid (60 ml, 0.1 mol/l) at room temperature and the resulting solution stirred for 10 minutes.

Subsequently, hexadecyltrimethylammonium chloride (0.64 g) was added and the thus obtained mixture was stirred at room temperature for 30 minutes. To this mixture, a solution of sodium orthovanadate dodecahydrate (8 g) in water (40 ml) was added and the resulting mixture was stirred at room temperature for 24 hours. This mixture was concentrated under reduced pressure in a rotary evaporator and dried at 100° C. for 4 hours.

Example 6

Preparation of $C_{16}H_{33}(CH_3)_3N^+[ZrVO_4]^-$ (Zr—V catalyst)

The Zr—V catalyst was prepared using the procedure of example 5, except that barium chloride dehydrate was replaced with zirconium nitrate pentahydrate.

Example 7

Preparation of $C_{16}H_{33}(CH_3)_3N^+[NaVO_4]^-$ (Na—V catalyst)

The Na—V catalyst was prepared using the procedure of example 4, except that iron(III) nitrate nonahydrate was replaced with sodium chloride (0.12 g).

Example 8

Preparation of $(C_{16}H_{33}(CH_3)_3N^+)_3[Al(VO_4)_2]^{3-}$ (Al—V catalyst)

The Na—V catalyst was prepared using the procedure of example 4, except that iron(III) nitrate nonahydrate was replaced with aluminum nitrate (0.75 g).

Comparative Example 1

Preparation of $C_{16}H_{33}(CH_3)_3N^+[NaWO_4]^-$ (Na—W catalyst)

Sodium chloride (0.1 g) was placed in a 100 ml flask, dissolved in nitric acid (30 ml, 0.1 mol/l) and the resulting solution was stirred for 10 minutes. Subsequently, a solution of sodium tungstate dehydrate (3.3 g) in 20 ml water was added and the thus obtained suspension was stirred for 20 minutes. Following, hexadecyltrimethylammonium chloride (0.32 g) was added and the resulting mixture was stirred at room temperature for 24 hours. The suspension was filtered, and the wet filter cake was dried at 60° C. for 4 hours.

Comparative Example 2

Preparation of $C_{16}H_{33}(CH_3)_3N^+[Mg_{0.5}WO_4]^-$ (Mg—W catalyst)

Magnesium nitrate hexahydrate (0.225 g) was placed in a 100 ml flask, dissolved in nitric acid (30 ml, 0.1 mol/l) and the resulting solution was stirred for 10 minutes. Subsequently, a solution of sodium tungstate dehydrate (3.3 g) in 20 ml water was added and the thus obtained suspension was stirred for 10 minutes. Following, hexadecyltrimethylammonium chloride (0.32 g) was added and the resulting mixture was stirred at room temperature for 24 hours. The suspension was filtered, and the wet filter cake was dried at 60° C. for 4 hours.

Comparative Example 3

Preparation of $C_{16}H_{33}(CH_3)_3N^+[Al(WO_4)_2]^-$ (Al—W catalyst)

The Al—W catalyst was prepared using the procedure of comparative example 2, except that magnesium nitrate hexahydrate was replaced with aluminum nitrate (0.75 g).

Comparative Example 4

Preparation of $C_{16}H_{33}(CH_3)_3N^+[Cu_{0.5}WO_4]^-$ (Cu—W catalyst)

Cupric nitrate (0.69 g) was placed in a 100 ml flask, dissolved in nitric acid (60 ml, 0.1 mol/l) and the resulting solution was stirred for 10 minutes. Subsequently, a solution of sodium tungstate dehydrate (6.6 g) in 40 ml water was added and the thus obtained suspension was stirred for 10 minutes. Following, hexadecyltrimethylammonium chloride (0.64 g) was added and the resulting mixture was stirred at room temperature for 24 hours. The suspension was filtered, and the wet filter cake was dried at 60° C. for 4 hours.

II. Catalysts Activities in Oxidation of Methylmercaptan with Hydrogen Peroxide to Dimethyldisulfide and Methansulfonic Acid

Comparative Example 5

Oxidation with the Na—W Catalyst

A solution of methylmercaptan in acetonitrile (77 g, 13.5%) was placed in a three-neck flask and 0.12 g of the Mg—W catalyst of comparative example 1 was added. The thus obtained reaction mixture was stirred at room temperature and hydrogen peroxide solution (99.7 g) was added dropwise at a temperature of less 40° C. within one hour. The resulting mixture was stirred at room temperature for 24 hours. The solvent was removed under reduced pressure using a rotary evaporator. The yield for methanesulfonic acid was 47.5% and the yield for sulfuric acid was 1.1%.

Comparative Example 6

Oxidation with the use of the Mg—W Catalyst

A solution of methyl mercaptan in acetonitrile (78 g, 16.5%) was placed in a three-neck flask and 0.15 g of the Mg—W catalyst of comparative example 2 was added. The thus obtained reaction mixture was stirred at room temperature and a hydrogen peroxide solution (122.4 g) was added dropwise at a temperature of less 40° C. within one hour. The resulting mixture was stirred at room temperature for 24 hours. The solvent was removed under reduced pressure using a rotary evaporator. The yield for methylsulfonic acid was 37.7% and the yield for sulfuric acid was 0.6%.

Comparative Example 7

Oxidation with the Al—W Catalyst

A solution of methylmercaptan in acetonitrile (77 g, 13.5% in acetonitrile) was placed in a three-neck flask and 0.12 g of the Al—W catalyst of comparative example 3 was added at room temperature. The thus obtained reaction mixture was stirred at room temperature and 99.8 g of a hydrogen peroxide solution was added dropwise at a temperature of less 40° C. over a period of one hour. The resulting mixture was stirred at room temperature for 24 hours. The solvent was removed under reduced pressure using a rotary evaporator. The yield for methanesulfonic acid was 41.7% and the yield for sulfuric acid was 1%.

Comparative Example 8

Oxidation with the use of the Cu—W Catalyst

A solution of methylmercaptan in acetonitrile (78 g, 16.5% in acetonitrile) was placed in a three-neck flask and 0.15 g of the Cu—W catalyst of comparative example 4 was added. The thus obtained reaction mixture was stirred at room temperature and a hydrogen peroxide solution (99.8 g) was added dropwise at a temperature of less 40° C. over a period of one hour. The resulting mixture was stirred at room temperature for 24 hours. The solvent was removed under reduced pressure using a rotary evaporator. The yield for methylsulfonic acid was 41.7% and the yield for sulfuric acid was 1%.

Example 9

Oxidation with the use of the Mg—V Catalyst

A solution of methyl mercaptan in acetonitrile (78 g, 16.5%) was placed in a three-neck flask and the Mg—V catalyst of example 1 (0.12 g) was added. The thus obtained reaction mixture was stirred at room temperature and hydrogen peroxide solution (122.5 g) was added dropwise at a temperature of less 40° C. over a period of one hour. The resulting mixture was stirred at room temperature for 24 hours. The solvent was removed under reduced pressure using a rotary evaporator. The yield for methanesulfonic acid was 63.9% and the yield for sulfuric acid was 0.4%.

TABLE 1

Results of the comparative examples 5 to 8 and of example 9

| Example | Catalyst | T [° C.] | Yield [%] MSA | $H_2SO_4$ |
|---|---|---|---|---|
| comp. example 5 | $C_{16}H_{33}(CH_3)_3N^+[NaWO_4]^-$ | 40 | 47.5 | 1.1 |
| comp. example 6 | $C_{16}H_{33}(CH_3)_3N^+[Mg_{0.5}WO_4]^-$ | 40 | 37.7 | 0.6 |
| comp. example 7 | $(C_{16}H_{33}(CH_3)_3N^+)_3[Al(WO_4)_2]^-$ | 40 | 41.7 | 1 |
| comp. example 8 | $C_{16}H_{33}(CH_3)_3N^+[Cu_{0.5}WO_4]^-$ | 40 | 41.7 | 1 |
| example 9 | $C_{16}H_{33}(CH_3)_3N^+[MgVO_4]^-$ | 40 | 63.9 | 0.4 |

III. Catalysts Activities in the Oxidation of Dimethyldisulfide with Oxygen to Methanesulfonic Acid Comparative Example 9

Without a Catalyst Under Oxygen Atmosphere (10 Bar)

A reaction mixture of dimethyldisulfide (15.02 g) and acetonitrile (150 g) was placed in a 500 ml autoclave and stirred at 90° C. under an oxygen atmosphere (10 bar) for 24 hours. The conversion of dimethyldisulfide was 4.4% (based on results obtained through gas chromatography) and the yield for the formation of methanesulfonic acid was 0.88%.

Comparative Example 10

Oxidation without a Catalyst Under Oxygen Atmosphere (40 Bar)

A reaction mixture of dimethyldisulfide (15.14 g) and acetonitrile (150 g) was placed in a 500 ml autoclave and stirred at 90° C. under an oxygen atmosphere (40 bar) for 24 hours. The conversion of dimethyldisulfide was 0.4% (based on results obtained through gas chromatography) and the yield for the formation of methanesulfonic acid was 0.87%.

Example 10

Oxidation using the Mg—V Catalyst Under Oxygen Atmosphere (10 Bar)

A reaction mixture of dimethyldisulfide (15.18 g), acetonitrile (153 g) and the Mg—V catalyst of example 1 (0.15 g) was placed in a 500 ml autoclave and stirred at 90° C. under an oxygen atmosphere (10 bar) for 24 hours. The conversion of dimethyldisulfide was 73% (based on results obtained through gas chromatography) and the yield for the formation of methanesulfonic acid was 53.7%.

Example 11

Oxidation using the Mg—V Catalyst Under Oxygen Atmosphere (40 Bar)

A reaction mixture of dimethyldisulfide (15.2 g), acetonitrile (150 g) and the Mg—V catalyst of example 1 (0.15 g) was placed in a 500 ml autoclave and stirred at 90° C. under an oxygen atmosphere (40 bar) for 24 hours. The conversion of dimethyldisulfide was 73% (based on results obtained through gas chromatography) and the yield for the formation of methanesulfonic acid was 56%.

Example 12

Oxidation using the Co—V Catalyst Under Oxygen Atmosphere (40 Bar)

A reaction mixture of dimethyldisulfide (15.14 g), acetonitrile (150 g) and the Co—V catalyst of example 2 (0.15 g) was placed in a 500 ml autoclave and stirred at 90° C. under an oxygen atmosphere (40 bar) for 24 hours. The conversion of dimethyldisulfide was 16% (based on results obtained through gas chromatography) and the yield for the formation of methanesulfonic acid was 8.7%.

Example 13

Oxidation using the Cu—V Catalyst Under Oxygen Atmosphere (40 Bar)

A reaction mixture of dimethyldisulfide (15 g), acetonitrile (150 g) and the Cu—V catalyst of example 3 (0.15 g) was placed in a 500 ml autoclave and stirred at 90° C. under an oxygen atmosphere (40 bar) for 24 hours. The conversion of dimethyldisulfide was 37% (based on results obtained through gas chromatography) and the yield for the formation of methanesulfonic acid was 22.4%.

Example 14

Oxidation using the Fe—V Catalyst Under Oxygen Atmosphere (40 Bar)

A reaction mixture of dimethyldisulfide (15.02 g), acetonitrile (150.34 g) and the Fe—V catalyst of example 4 (0.15 g) was placed in a 500 ml autoclave and stirred at 90° C. under an oxygen atmosphere (40 bar) for 24 hours. The conversion of dimethyldisulfide was 20% (based on results obtained through gas chromatography) and the yield for the formation of methanesulfonic acid was 11.3%.

Example 15

Oxidation using the Ba—V Catalyst Under Oxygen Atmosphere (40 Bar)

A reaction mixture of dimethyldisulfide (15.02 g), acetonitrile (150.1 g) and the Ba—V catalyst of example 5 (0.15 g) was placed in a 500 ml autoclave and stirred at 90° C. under an oxygen atmosphere (40 bar) for 24 hours. The conversion of dimethyldisulfide was 32% (based on results obtained through gas chromatography) and the yield for the formation of methanesulfonic acid was 10.2%.

Example 16

Oxidation using the Zr—V Catalyst Under Oxygen Atmosphere (40 Bar)

A reaction mixture of dimethyldisulfide (15.14 g), acetonitrile (150 g) and the Zr—V catalyst of example 6 (0.15 g) was placed in a 500 ml autoclave and stirred at 90° C. under an oxygen atmosphere (40 bar) for 24 hours. The conversion of dimethyldisulfide was 11% (based on results obtained through gas chromatography) and the yield for the formation of methanesulfonic acid was 6.5%.

TABLE 2

Results of the comparative examples 9 and 10 and of the examples 10 to 16

| Example | Catalyst | T [° C.] | p($O_2$) [bar] | $C_{DMDS}$ [%] | Yield [%] MSA | Yield [%] $H_2SO_4$ |
|---|---|---|---|---|---|---|
| comp. example 9 | — | 90 | 10 | 4.4 | 0.88 | 0 |
| comp. example 10 | — | 90 | 40 | 0.4 | 0.87 | 0 |
| example 10 | $C_{16}H_{33}(CH_3)_3N^+[MgVO_4]^-$ | 90 | 10 | 73 | 53.7 | 0.03 |
| example 11 | $C_{16}H_{33}(CH_3)_3N^+[MgVO_4]^-$ | 90 | 40 | 73 | 56 | 0.2 |
| example 12 | $C_{16}H_{33}(CH_3)_3N^+[CoVO_4]^-$ | 90 | 40 | 16 | 8.7 | 0 |
| example 13 | $C_{16}H_{33}(CH_3)_3N^+[CuVO_4]^-$ | 90 | 40 | 37 | 22.4 | 0.72 |
| example 14 | $C_{16}H_{33}(CH_3)_3N^+[FeVO_4]^-$ | 90 | 40 | 20 | 11.3 | 0.16 |
| example 15 | $C_{16}H_{33}(CH_3)_3N^+[BaVO_4]^-$ | 90 | 40 | 32 | 10.2 | 0 |
| example 16 | $C_{16}H_{33}(CH_3)_3N^+[ZrVO_4]^-$ | 90 | 40 | 11 | 6.5 | 0 |

IV. Catalyst Activity in the Oxidation of Methylmercaptan with Oxygen to Dimethyldisulfide and Methanesulfonic Example 17

Oxidation using the Mg—V Catalyst

A solution of methylmercaptan in acetonitrile (9.1%, 150 g) was placed in a 500 ml autoclave and the Mg—V catalyst $C_{16}H_{33}(CH_3)_3N^+[MgVO_4]^-$ (0.15 g) was added at room temperature. The reaction mixture was stirred at 90° C. under an oxygen atmosphere (40 bar) for 24 hours. Following, the reaction mixture was cooled to room temperature and analyzed. The conversion of methylmercaptan was 71%; the yield for the formation of dimethyldisulfide was 40% and the yield for the formation of methansulfonic acid was 4.2%.

V. Catalyst Activity in the Oxidation of Dimethyldisulfide with Oxygen to Methanesulfonic at Different Oxygen Pressures Comparative Example 11

Oxidation without a Catalyst Under Oxygen Atmosphere (10 Bar)

A solution of dimethyldisulfide in acetonitrile (9.1%, 150 g) was placed in a 500 ml autoclave at room temperature. No catalyst was added to this solution. The reaction mixture was heated at 90° C. and stirred under oxygen atmosphere (10 bar) for 24 hours. Following, the reaction mixture was cooled to room temperature and analyzed. The yield for the formation of methanesulfonic acid was 0.9%.

Example 18

Oxidation using the Mg—V Catalyst at Reflux

A solution of dimethyldisulfide in acetonitrile (9%, 111 g) was placed in a three-neck flask and the Mg—V catalyst $C_{16}H_{33}(CH_3)_3N^+[MgVO_4]^-$ (0.15 g) was added. The resulting reaction mixture was heated at 80° C. under oxygen atmosphere (gas sparging with 40 ml/min to 60 ml/min) for 24 hours. Since the reaction was performed under oxygen flow, the reaction temperature was lower than the boiling point of acetonitrile. Thus, the reaction mixture was stirred under slight reflux. In this way a loss of dimethyldisulfide could be avoided. The yield for the formation of methansulfonic acid was 0.1% and the yield for the formation of sulfuric acid was 0.006%.

Example 19

Oxidation using the Mg—V Catalyst Under Oxygen Atmosphere (10 Bar)

A solution of dimethyldisulfide in acetonitrile (9.1%, 150 g) and the Mg—V catalyst $C_{16}H_{33}(CH_3)_3N^+[MgVO_4]^-$ (0.15 g) was placed in a 500 ml autoclave at room temperature. This reaction mixture heated at 90° C. and stirred under oxygen atmosphere (10 bar) for 24 hours. Following, the reaction mixture was cooled to room temperature and analyzed. The yield for the formation of methanesulfonic acid was 53.7% and the yield for the formation was 0.3%.

Example 20

Oxidation using the Mg—V Catalyst Under Oxygen Atmosphere (40 Bar)

A solution of dimethyldisulfide in acetonitrile (9.1%, 150 g) and the Mg—V catalyst $C_{16}H_{33}(CH_3)_3N^+[MgVO_4]^-$ (0.15 g) was placed in a 500 ml autoclave at room temperature. This reaction mixture heated at 90° C. and stirred under oxygen atmosphere (40 bar) for 24 hours. Following, the reaction mixture was cooled to room temperature and analyzed. The conversion of dimethyldisulfide was 73%; the yield for the formation of methanesulfonic acid was 55% and the yield for the formation was 0.2%.

Example 21

Oxidation using the Mg—V Catalyst Under Oxygen Atmosphere (40 Bar) with Water

A solution of dimethyldisulfide in acetonitrile (9.1%, 150 g), the Mg—V catalyst $C_{16}H_{33}(CH_3)_3N^+[MgVO_4]^-$ (0.15 g) and water (2.89 g) was placed in a 500 ml autoclave at room temperature. This reaction mixture heated at 90° C. and stirred under oxygen atmosphere (40 bar) for 24 hours. Following, the reaction mixture was cooled to room temperature and analyzed. The conversion of dimethyldisulfide was 96%; the yield for the formation of methanesulfonic acid was 92% and the yield for the formation was 0.4%.

TABLE 3

Results of comparative example 11 without catalyst and of the examples 18 to 21 with the Mg—V catalyst of example 1

| Examples | Reaction conditions | | | | Yield | | | other by-products |
|---|---|---|---|---|---|---|---|---|
| | Concentration | T [° C.] | p [bar] | t [h] | MSA [%] | H$_2$SO$_4$ [%] | S balance [%] | |
| comp. example 11 | 9.1% in CH$_3$CN | 90 | 10 | 24 | 0.88 | — | 97.1 | — |
| example 18 | 9.1% in CH$_3$CN | reflux | 1 | 24 | 0.1 | 0.006 | 6.5 | — |
| example 19 | 9.1% in CH$_3$CN | 90 | 10 | 24 | 53.7 | 0.03 | 81 | CH$_3$—SO$_2$—CH$_3$ CH$_3$—SO$_2$—SO$_2$—CH$_3$ |
| example 20 | 9.1% in CH$_3$CN | 90 | 40 | 24 | 55 | 0.2 | 81 | CH$_3$—SO$_2$—CH$_3$ CH$_3$—SO$_2$—SO$_2$—CH$_3$ |
| example 21 | 9.1% in CH$_3$CN + H$_2$O* | 90 | 40 | 24 | 92 | 0.4 | 82 | H$_2$SO$_3$ |

In context of the present invention the term S balance indicates the sulfur balance:

$$S\ balance = \frac{moles\ of\ total\ sulfur\ derivative\ (after\ reaction)}{moles\ of\ initial\ sulfur\ in\ raw\ material} =$$

$$\frac{\Sigma\ (moles\ of\ sulfur\ in\ the\ obtained\ products\ after\ reaction) + (moles\ of\ sulfur\ in\ the\ remaining\ educt\ after\ reaction)}{moles\ of\ sulfur\ in\ the\ educt\ before\ reaction}.$$

An S balance of 100% indicates that there is no loss of sulfur in the reaction. Thus, all the products and by-products could be completely recovered, identified and quantified.

The invention claimed is:

1. A catalyst according to general formula (I):

$$Q_a[M_b(VO_4)_c]^{a-} \quad (I),$$

wherein

Q is a quaternary ammonium cation of the general formula (II)

$$R^1R^2R^3R^4N^+ \quad (II),$$

wherein each of R$^1$, R$^2$, R$^3$ and R$^4$ is independently of each other a saturated C$_1$ to C$_{20}$ alkyl radical or an aromatic C$_5$ or C$_6$ radical with the proviso that at least one of R$^1$, R$^2$, R$^3$ and R$^4$ is a saturated C$_4$ to C$_{20}$ alkyl group, M is at least one metal selected from the group consisting of alkali metals, alkaline earth metals, group III metals and transition metals, V denotes vanadium, O denotes oxygen, a is an integer from 1 to 3, b is the integer 1 or 2, and c is the integer 1 or 2.

2. The catalyst according to claim 1, wherein Q is a quaternary ammonium cation according to the general formula (III):

$$(C_nH_{2n+1})_o(CH_3)_{4-o}N^+ \quad (III),$$

wherein n is an integer from 4 to 18, and o is an integer from 1 to 4.

3. The catalyst according to claim 2, wherein Q is selected from the group of quaternary ammonium cations consisting of (C$_4$H$_9$)$_4$N$^+$, (C$_4$H$_9$)$_3$(CH$_3$)N$^+$, (C$_4$H$_9$)$_2$(CH$_3$)$_2$N$^+$, (C$_4$H$_9$)(CH$_3$)$_3$N$^+$, (C$_8$H$_{17}$)$_4$N$^+$, (C$_8$H$_{17}$)$_3$(CH$_3$)N$^+$, (C$_8$H$_{17}$)$_2$(CH$_3$)$_2$N$^+$, (C$_8$H$_{17}$)(CH$_3$)$_3$N$^+$, (C$_{12}$H$_{25}$)$_4$N$^+$, (C$_{12}$H$_{25}$)$_3$(CH$_3$)N$^-$, (C$_{12}$H$_{25}$)$_2$(CH$_3$)$_2$N$^+$, (C$_{12}$H$_{25}$)(CH$_3$)$_3$N$^+$, (C$_{16}$H$_{33}$)$_4$N$^+$, (C$_{16}$H$_{33}$)$_3$(CH$_3$)N$^+$, (C$_{16}$H$_{33}$)$_2$(CH$_3$)$_2$N$^+$, (C$_{16}$H$_{33}$)(CH$_3$)$_3$N$^+$, (C$_{18}$H$_{37}$)$_4$N$^+$, (C$_{18}$H$_{27}$)$_3$(CH$_3$)N$^+$, (C$_{18}$H$_{37}$)$_2$(CH$_3$)$_2$N$^+$, (C$_{18}$H$_{37}$)(CH$_3$)$_3$N$^+$, ((C$_{18}$H$_{37}$)$_{75\%}$(C$_{16}$H$_{33}$)$_{25\%}$)$_2$(CH$_3$)$_2$N$^+$ and combinations thereof.

4. The catalyst according to claim 3, wherein Q is (C$_{16}$H$_{33}$)$_4$N$^+$, (C$_{16}$H$_{33}$)$_3$(CH$_3$)N$^+$, (C$_{16}$H$_{33}$)$_2$(CH$_3$)$_2$N$^+$, or (C$_{16}$H$_{33}$)(CH$_3$)$_3$N$^+$ or combinations thereof.

5. The catalyst according to claim 1, wherein the metal M is selected from the group consisting of Mg, Co, Cu, Fe, Ba, Zr and combinations thereof.

6. The catalyst according to claim 5, wherein the metal M is Mg.

7. The catalyst according to claim 5, wherein a is 1, b is 1 and c is 1.

8. The catalyst according to claim 6, wherein the catalyst is a compound of the formula C$_{16}$H$_{33}$(CH$_3$)$_3$)N$^+$[MgVO$_4$]$^-$.

9. The catalyst according to claim 1 that is suitable for oxidation reactions.

10. A method for the production of a catalyst according to claim 1, which comprises:

a) providing a solution of a salt of the metal M in nitric acid, b) adding a salt of the quaternary ammonium cation Q to the solution obtained in a), c) adding a solution of a salt of an orthovanadate to the solution obtained in b), d) stirring the solution obtained in c), e) concentrating the solution of d) under reduced pressure to give a catalytically active mass, and f) drying the catalytically active mass obtained in e).

11. The method according to claim 10, wherein the sequence of b) and c) is exchanged.

12. A method for oxidation of a sulfur containing hydrocarbon compound comprising contacting a catalyst according to claim 1 with at least one sulfur containing hydrocarbon compound.

13. The method according to claim 12 that comprises
oxidation of alkylmercaptan to dialkyldisulfide and/or at least one alkanesulfonic acid with oxygen or hydrogen peroxide as an oxidizing agent in the presence or absence of nitric acid, or
oxidation of dialkyldisulfide to alkanesulfonic acid with oxygen or hydrogen peroxide as oxidizing agent in the presence or absence of nitric acid or the oxidation of dialkylpolysulfide to alkanesulfonic acid with oxygen or hydrogen peroxide as oxidizing agent in the presence or absence of nitric acid.

14. The method according to claim 13, that comprises oxidation of methylmercaptan to dimethyldisulfide and/or methanesulfonic acid with oxygen or hydrogen peroxide as oxidizing agent in the presence or absence of nitric acid, or oxidation of dimethyldisulfide to methanesulfonic acid with oxygen or hydrogen peroxide as oxidizing agent in the presence or absence of nitric acid or the oxidation of dimethylpolysulfide to methanesulfonic acid with oxygen or hydrogen peroxide as oxidizing agent in the presence or absence of nitric acid.

15. A process for the preparation of alkanesulfonic acid comprising:
   a) providing a solution comprising a sulfur containing hydrocarbon compound and a catalyst according to claim 1 in an organic solvent,
   b) introducing oxygen or hydrogen peroxide into a reaction system, and
   c) stirring the resulting mixture.

16. The process according to claim 15, wherein water is added in an amount which is sufficient to give the desired alkanesulfonic acid.

17. The process according to claim 15, wherein the sulfur containing hydrocarbon compound is methylmercaptan or dimethyldisulfide.

18. The process according to claim 15, wherein the organic solvent is selected from the group consisting of optionally substituted alkanes, optionally substituted aromatic hydrocarbons, esters, ethers, ketones, alcohols, carboxylic acids, nitriles amides, sulfones, sulfoxides, alkanesulfonic acids and combinations thereof.

19. The process according to claim 15, wherein the process is performed at a pressure of from 10 bar to 120 bar.

20. The process according to claim 15, wherein the process is performed at a temperature of from 40° C. to 150° C.

21. A catalyst according to general formula (I):

$$Q_a[M_b(VO_4)_c]^{a-} \quad (I),$$

wherein

Q is a quaternary ammonium cation of the general formula (II)

$$R^1R^2R^3R^4N^1 \quad (II),$$

wherein each of $R^1$, $R^2$, $R^3$ and $R^4$ is independently of each other a saturated $C_1$ to $C_{20}$ alkyl radical or an aromatic $C_5$ or $C_6$ radical with the proviso that at least one of $R^1$, $R^2$, $R^3$ and $R^4$ is a saturated $C_4$ to $C_{20}$ alkyl group, M is at least one metal selected from the group consisting Mg, Co, Cu, Fe, Ba, Zr and combinations thereof, V denotes vanadium, O denotes oxygen, a is an integer from 1 to 3, b is the integer 1 or 2, and c is the integer 1 or 2.

22. The catalyst according to claim 21, wherein a is 1, b is 1 and c is 1.

* * * * *